United States Patent
Schiller et al.

(10) Patent No.: US 10,406,067 B2
(45) Date of Patent: Sep. 10, 2019

(54) APPARATUS FOR PROVIDING CARDIOPULMONARY RESUSCITATION AND APPLICATION AID

(71) Applicant: SCHILLER AG, Baar (CH)

(72) Inventors: Alfred Schiller, Aeugst a.A. (CH); Johann-Jakob Schmid, Rifferswil (CH); Roman Steiner, Aeugst a.A. (CH)

(73) Assignee: SCHILLER AG, Baar (CH)

( * ) Notice: Subject to any disclaimer, the term of this patent is extended or adjusted under 35 U.S.C. 154(b) by 611 days.

(21) Appl. No.: 14/442,237

(22) PCT Filed: Oct. 29, 2013

(86) PCT No.: PCT/EP2013/072596
§ 371 (c)(1),
(2) Date: May 12, 2015

(87) PCT Pub. No.: WO2014/075915
PCT Pub. Date: May 22, 2014

(65) Prior Publication Data
US 2016/0213559 A1    Jul. 28, 2016

(30) Foreign Application Priority Data
Nov. 13, 2012   (EP) .................................... 12192399

(51) Int. Cl.
*A61H 31/00* (2006.01)
*A61F 7/12* (2006.01)
(Continued)

(52) U.S. Cl.
CPC ............ *A61H 31/006* (2013.01); *A61F 7/12* (2013.01); *A61N 1/046* (2013.01); *A61N 1/39* (2013.01);
(Continued)

(58) Field of Classification Search
CPC ............ A61H 31/006; A61H 2031/003; A61H 2201/1238; A61H 2201/10;
(Continued)

(56) References Cited

U.S. PATENT DOCUMENTS 4,532,921 A   8/1985  von Torklus et al.
5,683,404 A   11/1997 Johnson
(Continued)

FOREIGN PATENT DOCUMENTS

CN    1226146 A     8/1999
CN    202063381 U   12/2011
(Continued)

OTHER PUBLICATIONS

Chinese Third Office Action issued in corresponding Chinese Patent Application No. 201380058748.0 dated May 22, 2017.
(Continued)

*Primary Examiner* — Steven O Douglas
(74) *Attorney, Agent, or Firm* — Davis & Bujold PLLC; Michael J. Bujold (57) ABSTRACT

An apparatus (1) for providing cardiopulmonary resuscitation by applying compressions to a chest of a patient (P). The apparatus (1) comprising a chest compression unit (10), in particular comprising automatic actuation, at least one band (20) to be passed around the patient's chest for maintaining the chest compression unit (10) in position on the patient's chest. At least one end of the band (20) is releasably connectable to the unit (10) or another band. The apparatus (1) is designed for pushing the band (20) underneath the patient's chest, in particular on the side where the patient contacts the ground (G). The apparatus (1) comprises or is connectable to an application aid (30), in functional connection with the band (20), fixable to or movable relative to the band and adapted to support pushing the band (20)
(Continued)

underneath the patient's chest. The application aid is stiffer than the band.

13 Claims, 5 Drawing Sheets

(51) Int. Cl.
*A61N 1/39* (2006.01)
*A61N 1/04* (2006.01)
*A61F 7/00* (2006.01)

(52) U.S. Cl.
CPC ....... *A61F 7/123* (2013.01); *A61F 2007/0075* (2013.01); *A61F 2007/0091* (2013.01); *A61F 2007/126* (2013.01); *A61H 2031/003* (2013.01); *A61H 2201/0214* (2013.01); *A61H 2201/10* (2013.01); *A61H 2201/1238* (2013.01)

(58) Field of Classification Search
CPC .. A61H 2201/0214; A61N 1/046; A61N 1/39; A61F 7/12; A61F 2007/0091; A61F 2007/126; A61F 7/123; A61F 2007/0075
See application file for complete search history.

(56) References Cited

U.S. PATENT DOCUMENTS

| | | | | |
|---|---|---|---|---|
| 6,066,106 A * | 5/2000 | Sherman | ............... | A61H 31/006 601/134 |
| 6,174,295 B1 * | 1/2001 | Cantrell | ................. | A61H 31/00 601/41 |
| 6,213,960 B1 * | 4/2001 | Sherman | ................ | A61H 31/00 601/41 |
| 6,367,478 B1 | 4/2002 | Riggs | | |
| 7,226,427 B2 * | 6/2007 | Steen | ................... | A61H 31/008 128/204.18 |
| 2003/0004445 A1 * | 1/2003 | Hall | ..................... | A61H 9/0078 601/41 |
| 2006/0272095 A1 | 12/2006 | Kornaker | | |
| 2007/0225623 A1 * | 9/2007 | Freeman | .............. | A61H 31/004 601/41 |
| 2012/0116272 A1 | 5/2012 | Hampton et al. | | |
| 2013/0324894 A1 * | 12/2013 | Herken | ................ | A61H 31/006 601/41 |

FOREIGN PATENT DOCUMENTS

| | | |
|---|---|---|
| GB | 2 140 694 A | 12/1984 |
| WO | 00/27334 A2 | 5/2000 |
| WO | 2007/011798 A2 | 1/2007 |
| WO | 2010/098892 A2 | 9/2010 |

OTHER PUBLICATIONS

International Search Report Corresponding to PCT/EP2013/072596 dated Mar. 24, 2014.
Written Opinion Corresponding to PCT/EP2013/072596 dated Mar. 24, 2014.
Chinese Office Action issued in corresponding Chinese Patent Application No. 201380058748.0 dated Mar. 28, 2016.

* cited by examiner

APPARATUS FOR PROVIDING CARDIOPULMONARY RESUSCITATION AND APPLICATION AID

FIELD OF THE INVENTION

The present invention relates to an apparatus, a kit and a method for providing cardiopulmonary resuscitation (CPR) by applying compressions to the chest of a patient to stimulate blood circulation. In particular, the apparatus, kit and method of the present invention comprises a chest compression unit and a band to be passed around the patient's chest to maintain the chest compression unit in position on the patient.

BACKGROUND OF THE INVENTION

Such artificial stimulation of the blood circulation is particularly indicated for a person suffering from a cardiovascular emergency such as cardiac arrest.

Apparatus for providing automatic or assisted cardiopulmonary resuscitation are known in the prior art.

An known apparatus is the LUCAS™ CPR provided by the company Physio-Control Inc./Jolife AB. The apparatus has three stiff pivotally arranged parts which can not easily be adapted.

to the body of the patient. As a further disadvantage, the patient has to be slightly lifted up for passing such arrangement around the patient's chest which is a problem for obese patients.

A further known apparatus is the AutoPulse® provided by Zoll Medical with a load-distributing band which is clamped above the patient and which applies compressions to the chest of a patient. The AutoPulse® requires a solid plate installed on the dorsal side of the patient, i.e. consequently underneath the patient. For the arrangement of the solid plate, the patient needs to be lifted up slightly.

WO 2010/098892 A2 discloses another apparatus for providing compressions to the chest of a patient to stimulate blood circulation. It comprises a flat, wide, substantially stiff belt to be passed around a patient's chest and to maintain the chest compression unit in position on the patient.

Such apparatus still has the disadvantage that stiffness of the band may cause additional pain to the patient. Furthermore, a stiff band may complicate the handling for the application of the CPR apparatus around the patient's chest.

SUMMARY OF THE INVENTION

It is therefore an object of the present invention to overcome the drawbacks of the prior art. It is particularly an object to provide an apparatus, kit and method for providing cardiopulmonary resuscitation with a facilitated handling for the application of such apparatus and minimized pain for the patient.

This object is solved by an apparatus, a kit and a method according to the characterizing portions of the independent claims.

The apparatus according to the present invention is used for providing cardiopulmonary resuscitation by applying compressions to the chest of a patient. It comprises a chest compression unit and at least one band to be passed around the patient's chest and to maintain the chest compression unit in position on the patient's chest.

The chest compression unit may comprise an automatic actuation.

Preferably, the chest compression unit comprises an actuator which is automatically energized electromechanically, hydraulically or pneumatically. The apparatus further has an application member for pressing against an application site of the patient.

The application site may typically be the sternum of the patient. Other sites might also be conceivable.

Preferably, the band is fixable to the application member of the chest compression unit.

Alternatively, the chest compression unit may be configured to be operated manually at the application site of the patient by a rescuer.

Preferably, the band consists of or comprises a textile material. This improves the comfort for the patient.

The chest compression unit preferably is releasably connectable with at least one end of the band. Preferably, one end of the band is firmly and pivotally attached to one end of the chest compression unit, e.g. by a mounting strap, while the other end of the band is releasably connectable to another end of the chest compression unit.

In another preferred embodiment, both ends are releasably connectable. Both ends comprise the same mounting strap, preferably constructed as an eyelet. On one end, the band is immovably connected to the mounting strap. On the other end, the band is connected forming a lace such as to tighten the band around the patient once attached on both ends to the compression unit.

The apparatus comprises an application aid. The application aid is sized and shaped to be placed and pushed underneath a patient. Such application aid is a portion in functional connection or connectable with the band and adapted to support pushing the band underneath the patient's chest. Since the band is relatively flexible it can not be easily pushed underneath the patient. The application aid enforces the band and thus allows pushing of a band without there being a need for lifting the patient. The application aid is preferably dimensioned such as a patient might lie completely on the application aid once the aid is pushed underneath. Preferably, the application aid is constructed such that the band is slidable through the application aid but the mounting strap is not. In a position of the application aid next to the mounting strap, the application aid can be pushed underneath the patient delivering the mounting strap and therewith the band underneath the patient or on the other side of the patient, respectively. Preferably the mounting strap not pushed with the application aid is already connected to the compression unit. After connecting the second mounting strap, the band can be tightened by pulling on the free end of the lace.

A CPR apparatus in functional connection with such an application aid thus advantageously facilitates the application of such apparatus regardless of the patient's physique.

Preferably, the application aid has stiffer properties than the band.

As comparably flexible band, i.e. a band with reduced stiffness, minimizes potential additional pain to the patient. The band nevertheless can be pushed underneath the patient by using the stiffer application aid.

The application aid may be fixable or fixed to the band by a fixation means. Such fixable application aid may have the form of a clasp. In particular, in this embodiment the application aid is fixed at one end of the band.

Alternatively, the application aid may be a separate part movable relative to the band during operation of the CPR apparatus. Such movable application aid may have the form of a sleeve.

Such movable application aid has the advantage that it allows sliding within the application aid during operation.

The application aid preferably comprises a length sufficient for pushing under a patient, i.e. typically a length of 20 to 35 cm.

Such length substantially corresponds to the contact area between patient and ground allowing pushing and receiving the belt underneath the patient.

According to a preferred embodiment of the invention, the application aid has thickness of preferably 0.5 to 2 cm.

The thickness is chosen for allowing pushing the application aid underneath the patient, while the application aid still guarantees sufficient stability of the application aid and slidability for the band within the application aid.

According to a first preferred embodiment, the application aid comprises at least a lower plate, an upper plate and at least one distance piece between lower and upper plate, wherein the at least one distance piece, the lower plate and the upper plate are designed to allow passing of the band between lower and upper plate in a sleeve like manner.

According to an alternative second embodiment the application aid is fixedly attached to the band, in particular at least at its end.

The application aid may be formed in one piece.

Alternatively, the application aid may be formed by at least two parts. Such parts may be the lower plate, the upper plate or the at least one distance piece. The lower plate, upper plate and distance piece may be shaped or segmented for adaption to the shape of the patient. A segmented application aid may have sufficient rigidity while still allowing adaptation to the patient.

In a further preferred embodiment of the invention, the friction coefficient of the application aid relative to the band is comparably low, preferably between 0.1 to 0.3μ.

Preferably, the application aid consists of or comprises a polymer and/or copolymer with thermoplastic, thermosetting and/or elastomeric properties.

The material of the application aid comprises comparably high anti-abrasive properties and/or impact resistance to advantageously guarantee the functionality of the application aid despite mechanical stress during usage.

It is further preferred that the material of the application aid comprises a comparably low moisture absorption of less than 0.05% at 23° C. Furthermore, it is preferred that the material of the application aid comprises a density of preferably 0.915 to 1.35 g/cm$^3$.

Further preferred material properties of the application aid are: tensile yield strength of preferably between 10 to 50 megapascal, tensile yield strength of preferably between 5 to 25% and a nominal elongation of break preferably higher than 50%.

The application aid may be fabricated e.g. by injection moulding, extrusion, deep-drawing or lamination.

In a further aspect of the invention there is provided an application aid for assisting application of an apparatus for providing cardiopulmonary resuscitation by applying compressions to the chest of a patient. The application aid can be functionally connectable to an apparatus as previously described. The application aid is sized and shaped to be placed underneath said patient, particularly where said patient contacts the ground. Furthermore, the application aid is sized and shaped to support pushing the band underneath said patient for maintaining a chest compression unit in position on said patient's chest.

In a further aspect of the invention there is provided a kit for providing cardiopulmonary resuscitation by applying compressions to the chest of a patient. Such kit comprises an apparatus for providing cardiovascular resuscitation and an application aid as previously described.

According to a preferred embodiment of the invention, the apparatus comprises a connecting means adapted to connect the chest compression unit with the band.

Preferably, at least one end of the band is releasably connectable with the chest compression unit or with another band by the connecting means, e.g. by a Velcro system, a hook/loop closure or a snap-in clip.

The compression unit might be pneumatically driven as disclosed in U.S. Pat. No. 7,060,041 B1 or known as e.g. "Weil™ Mini Chest Compressor". Gas from a gas container drives the compression unit. A cooling effect because of the change of the liquid to a gaseous state may occur at the pressurized gas container. The pressurized gas container may comprise a contact surface for cooling. Such means may be used for cooling of the patient's body.

During decompression of the gas by the gas pressure reducing means, adiabatic expansion of the gas may occur, thereby providing a cooling effect. Preferably, the gas pressure reducing means comprises a means for the retrieval of cold. Such means may be used for the cooling at an application site of the patient's body.

In a preferred embodiment the apparatus comprises and/or is connectable to a cooling unit. The cooling unit can be used to cool the body, especially the brain of the patient. It is known that by cooling the body of a patient who suffers from a cardiac arrest to about 33° C., the neurological subsequent damages are reduced.

The cooling unit might comprise a cannula with a branch. The branch has at least one outlet for coupling with the pressurized gas container. The cannula is preferably sized and shaped for introduction into the patient's nasopharynx, the patient's mouth, the patient's trachea or the patient's stomach and/or intestine and at least one outlet for coupling a pneumatic compressor assembly with the pressurized gas container. Preferably, the at least one cannula is from an essentially rod-like shape and can be functionally connected to the pressurized gas container either directly or by means of a flexible tube.

Preferably, the cannula is sized and shaped for introduction into the interior of blood vessels, in particular the vena cava. More preferably, the cannula is adapted as an intravascular expandable balloon and provided with a cooling contact surface. Even more preferably, the expandable balloon is designed to have a star-like shape after inflation which advantageously increases the cooling contact surface.

In a still further embodiment, the pressurized gas container and the at least one cannula are adapted to provide for adiabatic expansion of the gas or mixture of gases, in particular as shown in EP 11191745.6 (incorporated herein by reference).

Such an apparatus is effective at cooling the brain or other internal areas or organs of a patient, particularly in case of cardiac arrest, acute myocardial infarction, ischemic stroke traumatic injury or neurogenic fever.

Thus, gases such as carbon dioxide allowing a combination of operating a pneumatic compressor assembly and cooling are most preferred. However, other gases effective substantially for the former or latter are advantageous as well.

Alternatively, the cooling unit might comprise an inflatable bag. The inflatable bag comprises a substantially closed sheath adapted to form an outer cooling contact surface upon inflation, and whereby the pressurized gas container and the inflatable bag are adapted to provide a cooling effect in the bag upon release of gas, e.g. by adiabatic expansion of the gas or mixture of gases.

Such inflatable bag with an outer cooling contact surface has the advantage that upon adiabatic expansion external cooling of the patient's body is achieved while the chest of the patient is still available e.g. for applying chest compressions.

WO 2006/000006 A2 proposes external cooling of a patient by means of an inflatable bag and a pressurized gas container storing liquid air, wherein, however, the inflatable bag fully envelopes the patient resulting in a direct contact between vaporized liquid air and the patient.

Preferably, the inflatable bag is adapted to form a tub upon inflation to surround substantially the patient on the rear and lateral side leaving the head and arms outside. Such a form of the inflatable bag has the advantage that the arms are available for intravenous liquid administration. More preferably, the inflatable bag is formed as sleeveless vest to be wrapped around the patient.

The pressurized gas container and the inflatable bag might be functionally connected either directly or by means of a flexible tube. Even more preferably, the pressurized gas container and the inflatable bag are adapted to provide for adiabatic expansion of the gas or mixture of gases stored in liquid form.

Further, at least one tube might be arranged within the bag, in particular at the walls of the bag, and the at least one tube is inflatable upon release of gas from the pressurized gas container. Preferably, the tube comprises at least one opening which is adapted to enable an adiabatic expansion of the gas when exiting the tube through the opening thereby providing a cooling effect.

Cooling of the bag may be achieved upon release of the gas, e.g. $CO_2$, into the bag and/or such tube within the bag comprising at least one opening adapted to enable adiabatic expansion of the gas. The bag may be inflated by pressurized gas from the pressurized gas container and/or additionally inflated by a pressurized gas from an additional gas source.

Alternatively the compression unit and the cooling unit are electrically driven. In electrically driven cooling units, electricity is used to pump the heat according to the Peltier effect. The cooling unit may comprise a bag or a cannula as described for the pneumatic driven cooling unit.

In a further preferred embodiment of the invention, the apparatus comprises and/or is connectable to a defibrillator.

The purpose of applying compressions to the chest of a patient during cardiopulmonary resuscitation (CPR) is to restore partial flow of oxygenated blood to the brain and heart. CPR alone is unlikely to restart the heart in case of ventricular fibrillation. Administration of one or several electric shocks to the patient's heart by a defibrillator is usually needed in order to restore a heart rhythm. Thus, a combined use of the apparatus with a defibrillator is advantageous.

In a still further preferred embodiment of the invention, the band comprises and/or is connectable to at least two electrode pads of the defibrillator.

Preferably, the at least two electrode pads are autonomous units connectable to the band or are directly integrated into the band. The at least two electrode pads may be designed to adhere at the patient's body. This reduces the displacement of the electrode pads of the defibrillator during chest compression.

By arranging the electrode pads at and/or in the band, the electrode pads are automatically positioned when applying the band for CPR. This leads to a quicker application of the electrodes and ensures a proper positioning.

In a preferred embodiment the chest compression unit, the defibrillator and a possible cooling unit are arranged or arrangeable in a common housing. With a construction within one housing, the CPR means, cooling means and defibrillation means are all stored together. There is only one device needed, to fulfill the different tasks. The device can therefore perform Chest compression with the CPR means, cooling the body with the cooling means and provide a shock to a patient's heart with the defibrillation means.

The different means do comprise parts which are not located inside the housing in order to fulfill their function. A piston of the CPR means has to be at least partly arranged outside the housing and in contact with a patient's chest in order to apply a compression to the chest. Some parts as e.g. a cannula or a bag of the cooling means have to be in direct contact with the body of the patient in order to cool it. And also the shock delivering parts, preferably electrical pads, of the defibrillating means have to be in contact with the body to deliver the shock to the patient's heart.

The main body of the CPR means, the cooling means, and the defibrillation means, comprising the electrical and/or the mechanical controlling unit are located inside the one housing.

In an embodiment with one housing, the chest compression unit and the cooling means are preferably electrically driven. An electrically driven chest compression unit has the advantage that no pressurized gas container is needed as it is in pneumatic chest compression units. Therefore, the embodiment can have much smaller dimensions. In a preferred embodiment the whole construction comprising the three different means is about 450 g. Such an embodiment might replace the defibrillators used in public places not able too cool or to exhibit chest compression.

Preferably, the chest compression unit, the defibrillator and the possible cooling means are all controlled by a common processor. With a common processor, the different tasks are all regulated from the same processor, therewith, a small and simple construction can be achieved.

Alternatively, every means comprises its own regulating processor. If the different means comprise their own processor, the means need further communication units. The communication units are needed for the chest compression unit, the cooling means and the defibrillator to work in concert.

Further, the apparatus preferably comprises an ECG measurement unit adapted to analyze ECG signals influenced by the chest compression. Preferably, the processor is adapted to use a specific analysis algorithm adapted for diagnosing the presence of a shockable rhythm during CPR if the chest compression is detected by said sensor.

The chest compression pulses from the actuator of the pneumatic compressor assembly cause artifact signals regularly, i.e. in substantially constant time intervals. Preferably, such analysis algorithm for diagnosing the presence of a shockable rhythm during CPR is able to detect shockable heart rhythms e.g. based on the regularity of the generated artifacts. Preferably, the processor comprises signal processing system, in particular a signal processing system, processing the incoming signals continuously with the aid of the analysis algorithm.

Such an analysis algorithm compensating ECG signals made on the chest compressions during CPR for diagnosing presence and time of shockable rhythms has been described in U.S. Pat. No. 6,287,328. A further way of minimizing signal disturbances during CPR is disclosed in U.S. Pat. No. 6,807,442.

Algorithms for analyzing artifact signals based on the compressions to the chest are usually performed on several ECG tests for diagnosing artifact signals.

Alternatively or additionally the direct measurement of the actuation of compressions by the actuator during CPR, preferably by a sensor is performed. The direct measurement of the actuation compression is easier and less error-prone than measurement on the patient and allows the operation of cardiovascular resuscitation and defibrillation in one apparatus.

According to a further aspect of the invention there is provided a method for preparing a patient before providing cardiopulmonary resuscitation by applying compressions to the chest of a patient. An application aid, in particular an application of an apparatus as previously described, is provided and placed underneath the patient's chest, in particular where the patient's chest contacts the ground. A band is pushed underneath the patient by using the application aid At least one end of the band is connected with a chest compression unit for maintaining the chest compression unit in position on the patient's chest during operation. Afterward, the chest compression unit can be operated.

BRIEF DESCRIPTION OF THE DRAWINGS

The invention will be further outlined in the following with reference to preferred embodiments with drawings, without being limited thereto.

DESCRIPTION OF THE PREFERRED EMBODIMENTS

Figure 1:
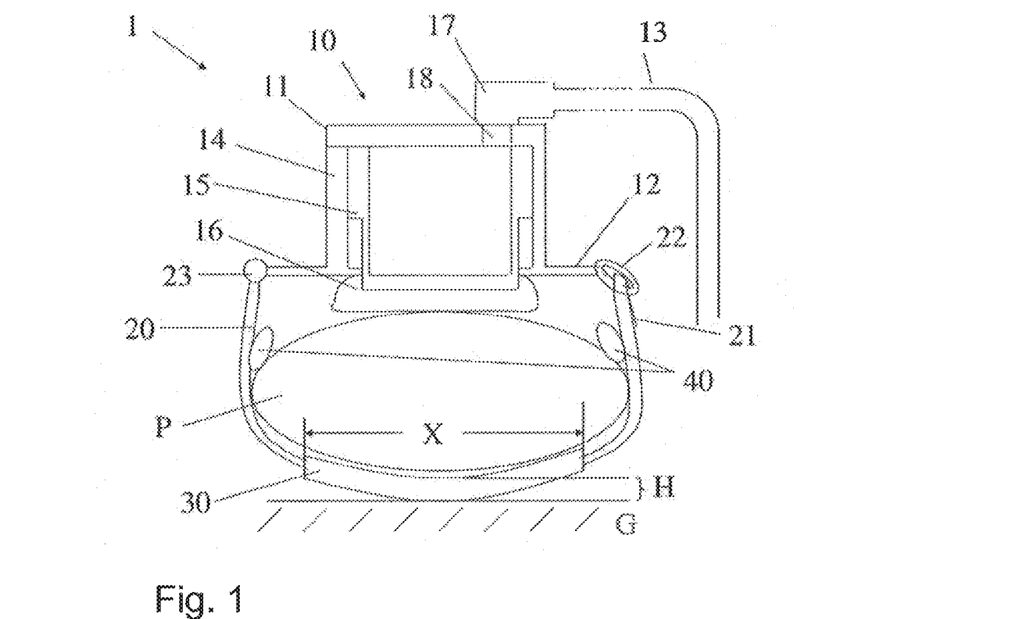
FIG. 1: shows a cross-sectional view of a first preferred embodiment of an apparatus according to the present invention with a movable application aid (sleeve)

FIG. 1 shows a cross-sectional view of a first preferred embodiment of an apparatus 1 for providing cardiovascular resuscitation. FIG. 1 shows a chest compression unit 10 with automatic actuation. The chest compression unit 10 may be designed substantially as shown in U.S. Pat. No. 7,060,041. It comprises an actuator 11 and an application member 12 for pressing against the sternum of a patient P. The actuator 11 is energized by a fluid compressor (not shown in FIG. 1) by means of a fluid tube 13 or alternatively electromechanically. FIG. 1 shows a band 20 which is passed around the patient's chest and maintains the chest compression unit 10 in position on the patient. The band 20 is at one end firmly attached to the application member 12 of the compression unit 10 by means of a mounting 23. The other end of the band 20 is releasably fixed to the application member 12 of the chest compression unit 10 by means of an eyelet 22 and Velcro fastener 21. A sleeve like application aid 30 is positioned between the patient's chest and the ground G. The band 20 is received by and movable relative to the application aid 30. The application aid 30 has preferably a length X of 30 cm and a thickness H of 5-20 mm. The application aid is made from a thermoplastic material, by injection molding. The actuator 11 includes a cylinder 14 and a piston 15 sliding within the cylinder 14. The cylinder 14 of the actuator 11 comprises a fluid inlet 18 allowing fluid to be supplied into a hollow space within the piston 15 and pressing the piston 15 downward thereby compressing the patient's chest. A pressing member 16 is fixed at the side of the cylinder 14 facing the patient P and functionally connected with the actuator 11. A connecting member 17 is arranged at the actuator 11 which provides an airtight connection between the fluid tube 13 and the fluid inlet 18. Return springs (not shown in FIG. 1) may be positioned between cylinder 14 and piston 15 to return the piston 15 back in the starting position after compression. Two electrode pads 40 are mounted on the inner surface and are in electric connection with a defibrillator (not shown in FIG. 1).

Figure 2:
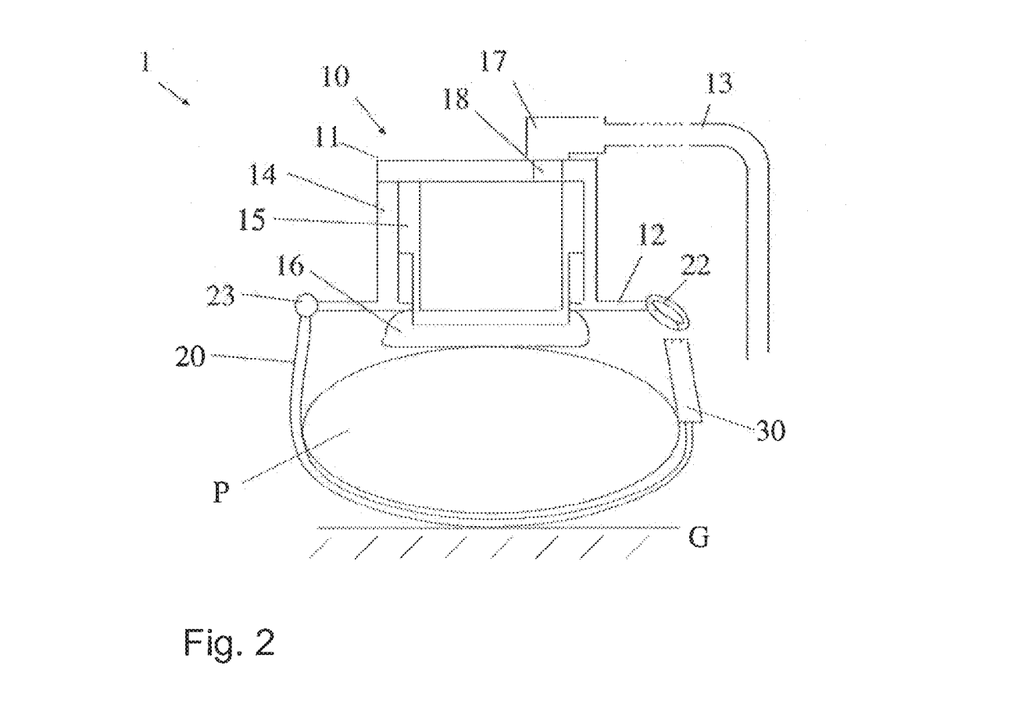
FIG. 2: shows a cross-sectional view of a second preferred embodiment of an apparatus according to the present invention with a fixable application aid (clasp)

FIG. 2 shows a cross-sectional view of a second preferred embodiment of an apparatus 1 according to the present invention. The application aid 30 is fixed at the end of the band 20 thereby comprising the form of a clasp. The band 20 may be fixed to the application member 12 of the chest compression unit 10 by application aid 30 in an appropriate eyelet 22.

Figure 3:
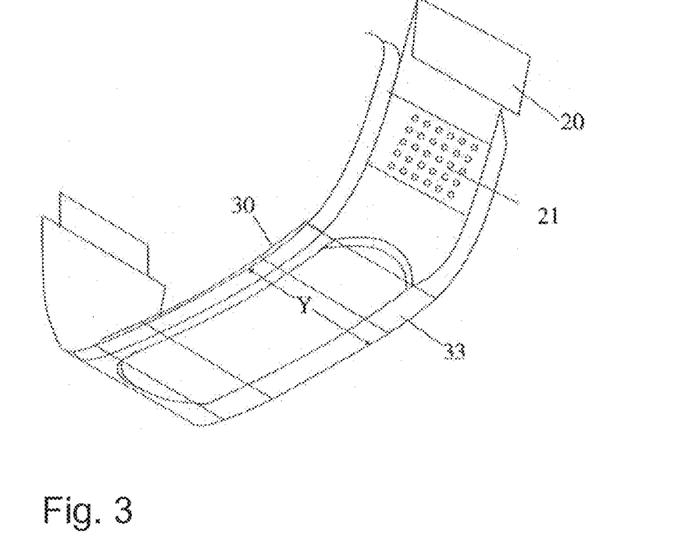
FIG. 3: shows a schematic drawing of the application aid of FIG. 1

FIG. 3 is a schematic drawing of the application aid 30 in the form of a sleeve which is movable relative to the band 20. FIG. 1 shows an application aid 30 including an upper plate 33 which is segmented in three parts to adapt to the shape of the body. The application aid 30 has preferably a width Y of 120-180 mm. FIG. 3 further shows the loop strap of Velcro fastener 21 to releasably fix the band 20 to the application member 12 of chest compression unit 10.

Figure 4:
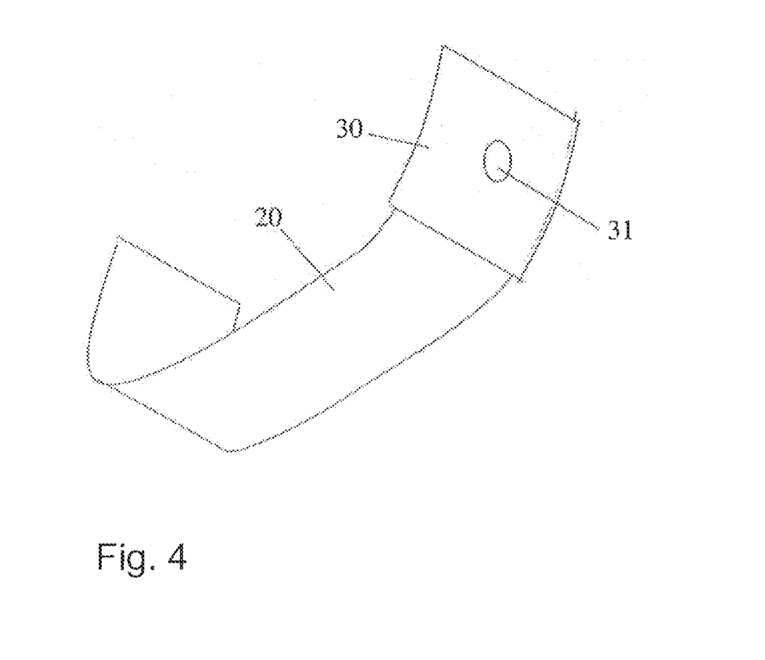
FIG. 4: shows a schematic drawing of the application aid of FIG. 2

FIG. 4 is a schematic drawing of the application aid 30 in the form of a clasp which is fixable to the application member 12 of the chest compression unit 10.

Figure 5:
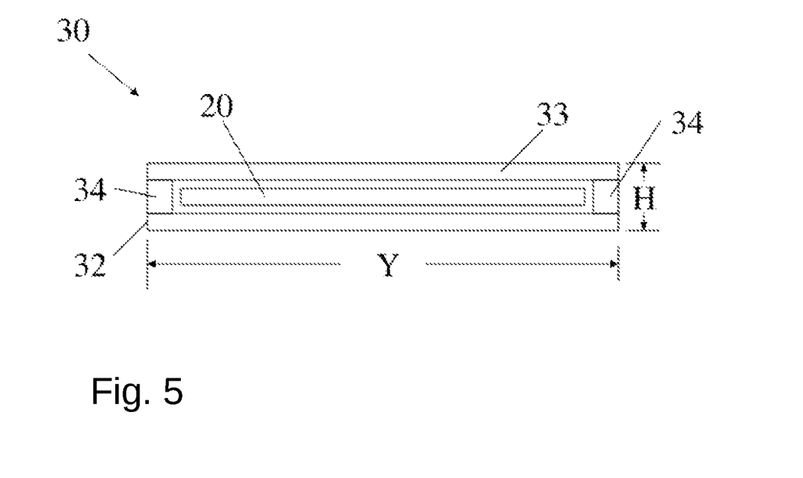
FIG. 5: shows a cross-sectional view through the application aid of FIG. 1.

FIG. 5 shows a cross-sectional view through the application aid 30 of FIGS. 1 and 2. The application aid comprises a lower plate 32 and an upper plate 33 which are distanced by two distance pieces 34. FIG. 5 further shows the band 20 which is slideably received between the lower plate 32 and the upper plate 33 of the application aid 30.

Figure 6:
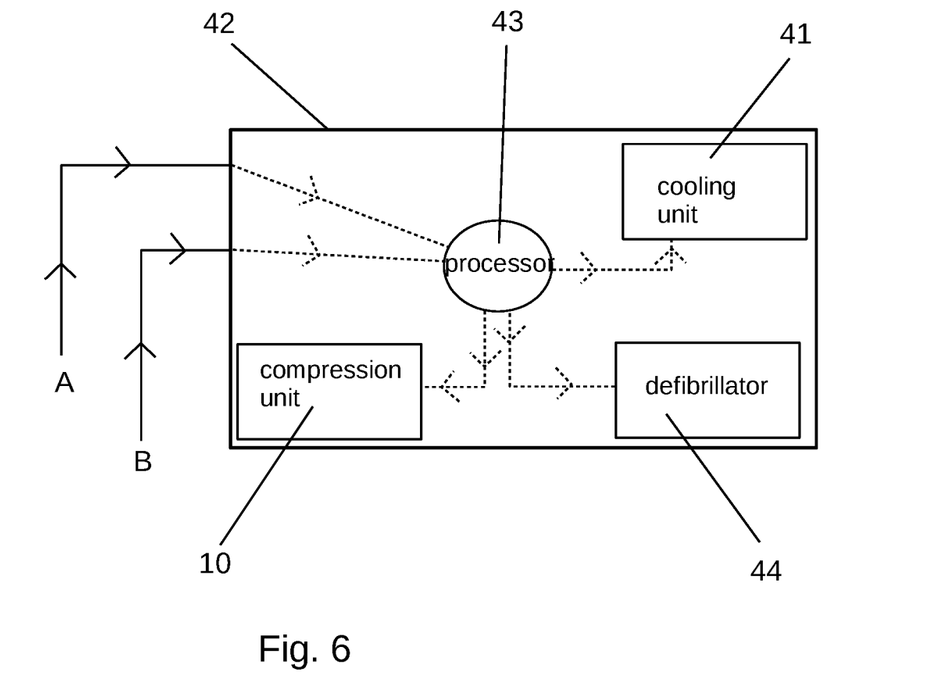
FIG. 6: shows a schematic view of various components arranged in a common housing.

FIG. 6 shows a compression unit 10, a defibrillator 44, and a cooling unit 41 in a common housing 42. The three compounds 10, 41, 44 are all electrically driven. A common processor 43 controls (dashed arrows) the three compounds 10, 41, 44. The common processor makes sure that the three compounds work in concert e.g. that no chest compression is performed during delivery of a shock.

Figure 7:
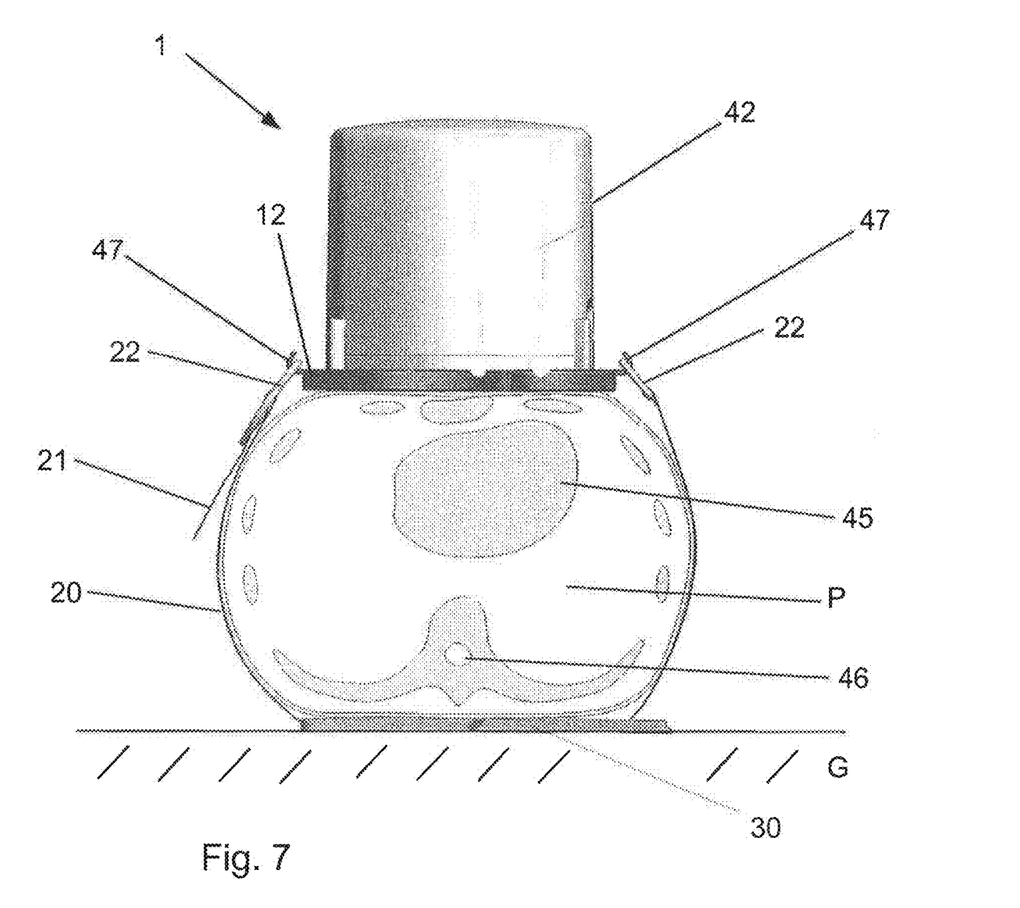
FIG. 7: shows a schematic view of a preferred embodiment of an apparatus and the application aid according to the present invention arranged on a patient.

FIG. 7 shows an apparatus 1 mounted on a patient P. The apparatus 1 comprises a common housing 42. In the common housing 42 is a compression unit (not shown), a defibrillator (not shown) and a cooling unit (not shown), and a processor (not shown). The apparatus 1 is fixed to the patient P with an application aid 30 and a band 20. The band 20 of the application aid 30 is releasably attached an application member 12. Counterparts 47 of the application member 47 are connected to two eyelets 22 fixed to both ends of the band 20. One eyelet 22 comprises a Velcro fastener 21 constructed as a lace. With the aid of the Velcro fastener 21, the band 20 is tightened around the patient P. The band 20 is moveable connected to the application aid 30. The application aid is constructed as an upper plate and a lower plate wherein the band 20 is between the two plates. During performing of chest compression, the application aid 30 lies between the ground G and the patient. The application aid 30 therefore is under the spine 46 of the patient. The application aid 30 provides a steady support under the patient and protects the spine as the spine cannot be bent too much.

Figure 8:
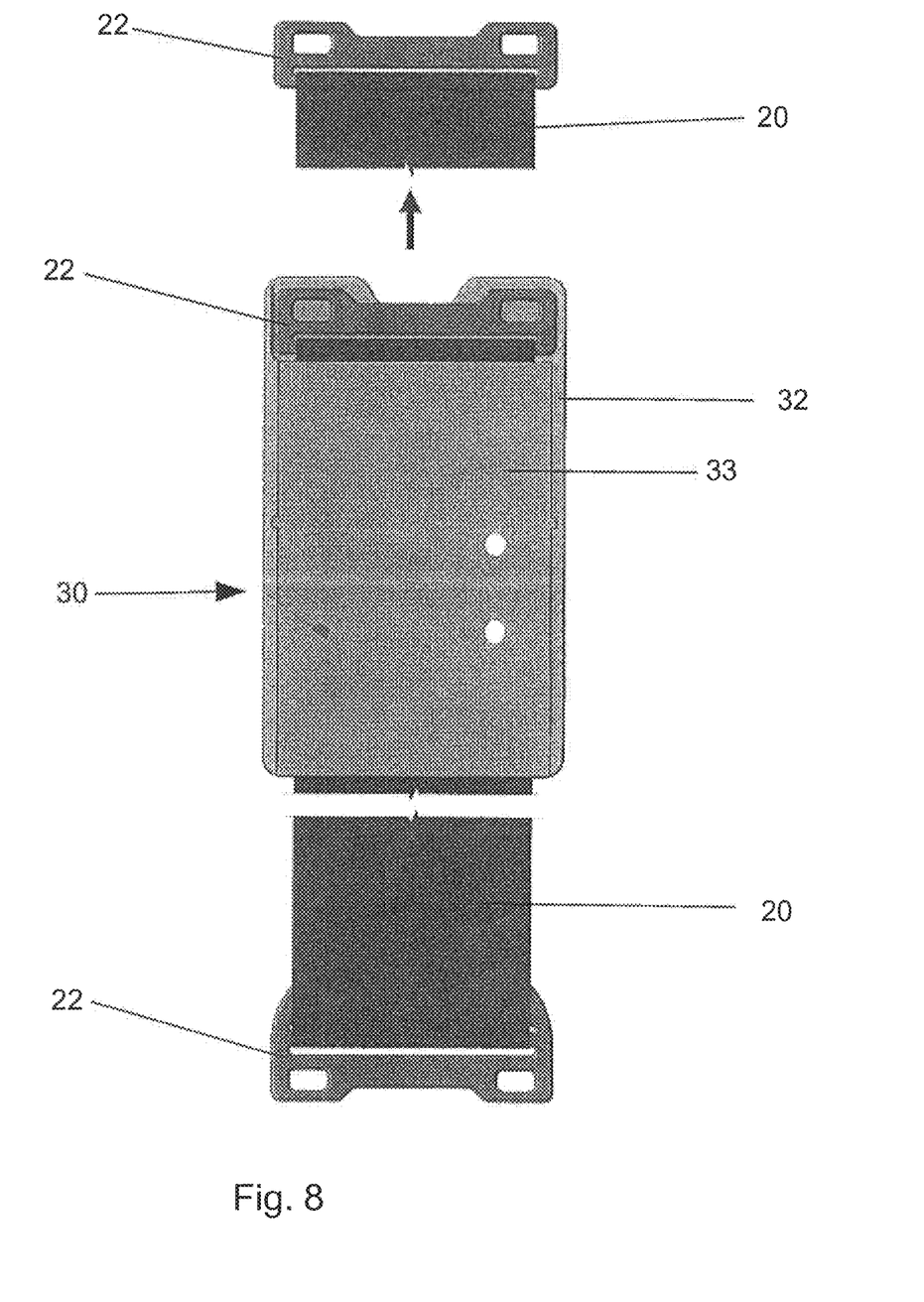
FIG. 8: shows a schematic view of the application aid of FIG. 7.

FIG. 8 shows the application aid 30 comprising the upper plate 33 and lower plate 32. The band 20 is mounted between the plates 33, 32. The band 20 can be moved through the application aid 30 until the eyelet 22 is in direct contact with the application aid 30. The eyelet 22 is thicker than the band 20 and can not move between the upper plate 33 and lower plate 32. In the position with the eyelet 22 in contact with the application aid 30, the other eyelet is fixed to the counterpart 47 and the application aid 30 is then pushed underneath the patient. The application aid 30 is pushed in the direction of the contacting eyelet 22 and therewith delivers the eyelet 22 and the band 20. When the application aid 30 is lying underneath the patient, the contacting eyelet 22 is on the other side of the patient. By pulling the eyelet 22, and attaching it to counterparts, the patient can be fixed to the application aid 30.

The invention claimed is:

1. An apparatus for providing cardiopulmonary resuscitation by applying compressions to a chest of a patient, said apparatus comprising:
   a chest compression unit including an automatic actuator, and
   at least one band adapted to be passed around a mid-section of the patient for maintaining said chest compression unit in position on said chest of the patient during use,
   wherein at least one end of the at least one band is releasably connectable to said chest compression unit, and
   the apparatus comprises an application aid in functional connection with said at least one band,
   said at least one band is receivable by said application aid and said application aid being movable relative to said at least one band and adapted to support passing said at least one band around the mid-section of the patient, and said application aid is stiffer than said at least one band, and
   said application aid is sleeve like and the actuator comprises a piston,
   said piston is connected to a pressing member, and said pressing member has a pressing surface placeable on the chest of the patient,
   said piston is moveable perpendicular to the pressing surface, and
   compression of the chest of the patient is only achievable by the piston and pressing member.

2. The apparatus according to claim 1, wherein said application aid has a length of 20 to 35 cm.

3. The apparatus according to claim 1, wherein said application aid has a thickness of 0.5 to 2 cm.

4. The apparatus according to claim 1, wherein said application aid comprises at least a lower plate, an upper plate and at least one distance piece between said lower and said upper plate, and said at least one distance piece, said lower and said upper plate are designed to allow passing of said at least one band between said lower and said upper plate.

5. The apparatus according to claim 1, wherein a friction coefficient of said application aid relative to said at least one band is between 0.1 and 0.3.

6. An application aid for assisting application of an apparatus for providing cardiopulmonary resuscitation by applying compressions to the chest of a patient, being functionally connectable to an apparatus according to claim 1, wherein the application aid is sleeve like and the application aid is sized and shaped:
   to be placed underneath said patient, and
   to support pushing a band underneath and around said chest of the patient for maintaining the chest compression unit in position on said patient's chest.

7. A kit for providing cardiopulmonary resuscitation by applying compressions to the chest of the patient, said kit comprising:
   an apparatus for providing cardiopulmonary resuscitation by applying compressions to a chest of a patient, said apparatus (1) comprising: a chest compression unit (10) including an automatic actuator, and at least one band adapted to be passed around said chest of the patient for maintaining said chest compression unit in position on said chest of the patient during use, wherein at least one end of the at least one band is releasably connectable to said chest compression unit, and the apparatus comprises an application aid in functional connection with said at least one band,
   wherein said at least one band is not adapted to compress or aid with the compression of the chest of the patient;
   said at least one band is receivable by said application aid and said application aid being movable relative to said at least one band and adapted to support pushing said at least one band underneath said chest of the patient, and said application aid is stiffer than said at least one band; and
   the application aid according to claim 6.

8. The apparatus according to claim 1, wherein the apparatus comprises a connecting means located between said chest compression unit and said at least one band adapted to connect said chest compression unit with said at least one band.

9. The apparatus according to claim 1, wherein the apparatus is connectable to a cooling unit.

10. The apparatus according to claim 1, wherein the apparatus is connectable to a defibrillator.

11. The apparatus according to claim 10, wherein said at least one band is connectable to at least two electrode pads of said defibrillator.

12. A method for preparing a patient for cardiopulmonary resuscitation, the method comprising the steps of:
   a) pushing an application aid according to claim 6 and a band underneath a chest of a patient, and
   b) connecting at least one end of said band with a chest compression unit for maintaining said chest compression unit in position on said chest of the patient during operation.

13. An apparatus for providing cardiopulmonary resuscitation by applying compressions to a chest of a patient, the apparatus comprising:
   a chest compression unit including an automatic actuator, and
   a band having a first end connected to the chest compression unit and a second end adapted to pass around mid-section of the patient and maintain the chest compression unit in position on the chest of the patient during use, wherein the second end of the band is releasably connectable to the chest compression unit space away from the first end which is connected to the chest compression unit, the apparatus comprises an application aid and the band is receivable by the application aid, the application aid is stiffer than the band and is movable relative to the band to facilitate passing the band around the mid-section of the patient, and the application aid is sleeve like, the actuator comprises a piston, the piston is connected to a pressing member and the pressing member has a pressing surface placeable on the chest of the patient, the piston is moveable perpendicular to the pressing surface, and compression of the chest of the patient is only achievable by the piston and pressing member.

* * * * *